(12) United States Patent
Kramer et al.

(10) Patent No.: US 8,952,047 B1
(45) Date of Patent: Feb. 10, 2015

(54) BETAINE COMPOUNDS

(71) Applicants: Ronald Kramer, Phoenix, AZ (US); Alexander Nikolaidis, New Kallikratia (GR)

(72) Inventors: Ronald Kramer, Phoenix, AZ (US); Alexander Nikolaidis, New Kallikratia (GR)

(73) Assignee: ThermoLife International, LLC, Phoenix, AZ (US)

( * ) Notice: Subject to any disclaimer, the term of this patent is extended or adjusted under 35 U.S.C. 154(b) by 0 days.

(21) Appl. No.: 14/065,367

(22) Filed: Oct. 28, 2013

Related U.S. Application Data

(63) Continuation of application No. 13/468,231, filed on May 10, 2012, now Pat. No. 8,569,369, which is a continuation-in-part of application No. 12/946,153, filed on Nov. 15, 2010, now Pat. No. 8,178,572, which is a continuation of application No. 12/336,938, filed on Dec. 17, 2008, now Pat. No. 8,034,836, which is a continuation of application No. 11/950,273, filed on Dec. 4, 2007, now Pat. No. 7,777,074, application No. 14/065,367, which is a continuation of application No. 13/465,947, filed on May 7, 2012, now Pat. No. 8,569,368, which is a continuation-in-part of application No. 12/946,114, filed on Nov. 15, 2010, now Pat. No. 8,183,288, which is a continuation of application No. 12/336,938, filed on Dec. 17, 2008, now Pat. No. 8,034,836, which is a continuation of application No. 11/950,273, filed on Dec. 4, 2007, now Pat. No. 7,777,074.

(60) Provisional application No. 60/973,229, filed on Sep. 18, 2007.

(51) Int. Cl.
*A61K 31/415* (2006.01)
*C07C 53/00* (2006.01)

(52) U.S. Cl.
USPC .......................................... 514/400; 562/512

(58) Field of Classification Search
USPC .......................................... 514/400; 562/512
See application file for complete search history.

(56) References Cited

U.S. PATENT DOCUMENTS

| | | | |
|---|---|---|---|
| 3,886,040 A | 5/1975 | Chibata et al. | |
| 3,997,659 A | 12/1976 | Knohl et al. | |
| 4,146,611 A | 3/1979 | Ondetti et al. | |
| 4,379,177 A | 4/1983 | McCoy et al. | |
| 4,743,614 A | 5/1988 | Terano et al. | |
| 4,996,067 A | 2/1991 | Kobayashi et al. | |
| 5,500,436 A | 3/1996 | Schonafinger et al. | |
| 5,543,430 A | 8/1996 | Kaesemeyer | |
| 5,679,704 A | 10/1997 | Schonafinger et al. | |
| 5,965,596 A | 10/1999 | Harris et al. | |
| 7,235,237 B2 | 6/2007 | Loscalzo et al. | |
| 7,777,074 B2 | 8/2010 | Kramer et al. | |
| 8,034,836 B2 | 10/2011 | Kramer et al. | |
| 8,048,921 B2 | 11/2011 | Kramer et al. | |
| 8,178,572 B2 | 5/2012 | Kramer et al. | |
| 8,183,288 B2 | 5/2012 | Kramer et al. | |
| 8,455,531 B2 | 6/2013 | Kramer et al. | |
| 8,466,187 B2 | 6/2013 | Kramer et al. | |
| 8,569,368 B2 | 10/2013 | Kramer et al. | |
| 8,569,369 B2 | 10/2013 | Kramer et al. | |
| 2002/0119933 A1 | 8/2002 | Butler et al. | |
| 2003/0119888 A1 | 6/2003 | Allen | |
| 2004/0097401 A1 | 5/2004 | Datta | |
| 2005/0287210 A1 | 12/2005 | Ron | |
| 2005/0288372 A1 | 12/2005 | Ron | |
| 2005/0288373 A1 | 12/2005 | Ron | |
| 2006/0029668 A1 | 2/2006 | Ron | |
| 2006/0142382 A1 | 6/2006 | Morimoto et al. | |
| 2006/0182815 A1 | 8/2006 | Gladwin et al. | |
| 2007/0154569 A1 | 7/2007 | Gladwin et al. | |

FOREIGN PATENT DOCUMENTS

| | | |
|---|---|---|
| CN | 1631539 | 6/2005 |
| EP | 1336602 | 8/2003 |
| GB | 2354441 | 3/2001 |
| WO | WO2006/124161 | 11/2006 |

OTHER PUBLICATIONS

Ilczyszyn et al. CAS: 145:83630, 2006.*
Godzisz et al. CAS: 137: 62989, 2002.*
Piccolo et al. CAS: 138: 137589, 2003.*
Bauer et al., "Vascular and Hemodynamic Differences between Organic Nitrates and Nitrites," Journal of Pharmacology and Experimental Therapeutics 280:326-331 (1997).
Niu et al., "Vasorelaxant effect of taurine is diminished by tetraethylammonium in rat isolated arteries," European Journal of Pharmacology 580:169-174 (2008).
Tan et al., "Taurine protects against low-density lipoprotein-induced endothelial dysfunction by the DDAH/ADMA pathway," Vascular Pharmacology 46:338-345 (2007).
Ahtee et al., "Taurine Biological Actions and Clinical Perspectives," J. Nutr. 116:2555-2556 (1986).
Bloomer et al., "Glycine propionyl-L-carnitine increases plasma nitrate/nitrite in resistance trained men," Journal of the International Society of Sports Nutrition 4(22):1-6 (2007).
Ramaswamy et al., "Vibrational spectroscopic studies of L-argininium dinitrate," J. Raman Spectrosc. 34:50-56 (2003).

(Continued)

*Primary Examiner* — Rei-tsang Shiao
(74) *Attorney, Agent, or Firm* — Booth Udall Fuller, PLC

(57) ABSTRACT

A Nitrate or Nitrite of a Betaine Compound disclosed. Also disclosed are a composition and a supplement formulation comprising at least one constituent selected from the group consisting of a Nitrate, a Nitrite, and both; and a Betaine Compound. The composition and supplement formulation may be formulated to deliver an effective amount of the constituents to prevent the development of nitrate tolerances, to increase bioabsorption of amino acids, or to increase the vasodilative characteristics of amino acids in a human or animal.

11 Claims, No Drawings

(56) References Cited

OTHER PUBLICATIONS

Rajkumar et al., "Infrared and Raman spectra of L-valine nitrate and L-leucine nitrate," J. Raman Spectrosc. 31:1107-1112 (2000).
Petrosyan et al., "L-Histidine nitrates," Journal of Molecular Structure 794:160-167 (2006).
Cromwell et al., "The Biosynthesis and Metabolism of Betaines in Plants," Biochem J. 55:189-192 (1953).
Basheva et al., "Role of Betaine as Foam Booster in the Presence of Silicone Oil Drops," Langmuir 16:1000-1013 (2000).
Danov et al., "Mixed Solutions of Anionic and Zwitterionic Surfactant (Betaine): Surface Tension Isotherms, Adsoprtion, and Relaxation Kinetics," Langmuir 20:5445-5453 (2004).
Xu et al., "Composite medical preparation for promoting hair growth," CAS: 143:103285 (2005).
Sridhar et al, "L-Aspartic Acid Nitrate-L-Aspartic Acid," Acta Cryst. E58:o1372-o1374 (2002).
Sridhar et al, "Bis (beta-alanine) hydrogen nitrate," Acta Cryst. E57:o1004-o1006 (2001).
Rao et al., "Structure and Conformational Aspects of the Nitrates of Amino Acids and Peptides. I. Crystal Structure of Glycylglycine Nitrate," Acta Cryst. B29:2379-2388 (1973).
Bauer et al., "Photochemical Generation of Nitric Oxide from Nitro-containing Compounds: Possible Relation to Vascular Photorelaxation Phenomena," Life Science 54(1):PL1-PL4 (1994).
Magg et al., "Nitrogenous Compounds in Sugarbeet Juices," Journal of the American Society of Sugar Beet Technologists 17(2):154-164 (1972).
Mostad et al., "Crystal and molecular structure of DL-methionine nitrate," CAS 104:197543 (1986).
Pradhan et al., "Effect of Anions on the Solubility of Zwitterionic Amino Acids," J. Chem. Eng. Data 45(1):140-143 (2000).
Terzyan et al., "L-Arginine Nitrates," Journal of Molecular Structure 687:111-117 (2004).
Stryer, Lubert, Biochemistry, Third Edition, W. H. Freeman and Co.: New York, 1988, pp. 16-23, 500-502, and 934-936.
Sastre et al., "Metabolism of agmatine in macrophages: modulation by lipopolysaccharide and inhibitory cytokines," Biochem. J. 330:1405-1409 (1998).
Ishii et al., "High glucose augments arginase activity and nitric oxide production in the renal cortex," Metabolism 53 (7):868-874 (2004).
Barger, G. (1914) The Simpler Natural Bases. In R.H.A. Plimmer & F.G. Hopkins (Eds.) Monographs on Biochemistry (pp. 157-163) Longmans, Green & Co., London.
Larsen et al., "Effects of dietary nitrate on oxygen cost during exercise," Acta Physiol 191:59-66 (2007).
Berge et al., "Pharmaceutical Salts," Journal of Pharmaceutical Sciences 66(1):1-18 (1977).
Jablecka et al., "The influence of two different doses of L-arginine oral supplementation on nitric oxide (NO) concentration and total antioxidant status (TAS) in atherosclerotic patients," Med Sci Monit 10(1):CR29-32 (2004).
Maynard et al., "High Levels of Dietary Carnosine Are Associated with Increased Concentrations of Carnosine and Histidine in Rat Soleus Muscle," J. Nutr. 131:287-290 (2001).
Ruel et al., "Modulation in Angiogenic Therapy randomized controlled trial," J Thorac Cardiovasc Surg 135:762-770 (2008).
Rytlewski et al., "Effects of oral L-arginine on the pulsatility indices of umbilical artery and middle cerebral artery in preterm labor," European Journal of Obstetrics & Gynecology and Reproductive Biology 138:23-28 (2008).
Schwedhelm et al., "Pharmacokinetic and pharmacodynamics properties of oral L-citrulline and L-arginine: impact on nitric oxide metabolism," Br J Clin Pharmacol 65(1):51-59 (2007).
Smith et al., "Nitric oxide precursors and congenital heart surgery: A randomized controlled trial of oral citrulline," J Thorac Cardioasc Surg 132:58-65 (2006).
Rytlewski et al., "Effects of prolonged oral supplementation with L-arginine on blood pressure and nitric oxide synthesis in preeclampsia," Eur J Clin Invest 35(1):32-37 (2005).
Ming et al., "Thrombin Stimulates Human Endothelial Arginase Enzymatic Activity via RhoA/ROCK Pathway," Circulation 110:3708-3714 (2004).
Romero et al., "Therapeutic Use of Citrulline in Cardiovascular Disease," Cardiovascular Drug Reviews 24 (3-4):275-290 (2006).
Oka et al., "A pilot study of L-arginine supplementation on functional capacity in peripheral arterial disease," Vascular Medicine 10:265-274 (2005).
Hayashi et al., "L-citrulline and L-arginine supplementation retards the progression of high-cholesterol-diet-induced atherosclerosis in rabbits," PNAS 102(38):13681-13686 (2005).
Grasemann et al., "Oral L-arginine supplementation in cystic fibrosis patients: a placebo-controlled study," Eur Respir J 25:62-68 (2005).
Boger, "The Pharmacodynamics of L-Arginine," J. Nutr. 137:1650S-1655S (2007).
Beghetti et al., "Nitric oxide precursors and congenital cardiac surgery: A randomized controlled trial of oral citrulline. Definition of pulmonary hypertension in Fontan circulation?" J Thorac Cardioasc Surg 132(6):1501-1502 (2006).
Takahashi et al., "Characterization of the influence of nitric oxide donors on intestinal absorption of macromolecules," International Journal of Pharmaceutics 286:89-97 (2004).
Fetih et al., "Nitric oxide donors can enhance the intestinal transport and absorption of insulin and [Asu1,7]-eel calcitonin in rats," Journal of Controlled Release 106:287-297 (2005).
Fetih et al., "Excellent Absorption Enhancing Characteristics of NO Donors for Improving the Intestinal Absorption of Poorly Absorbable Compound Compared with Conventional Absorption Enhancers," Drug Metab. Pharmacokinet. 21(3):222-229 (2006).
Aniya et al., "Evaluation of Nitric Oxide Formation from Nitrates in Pig Coronary Arteries," Jpn. J. Pharmacol. 71:101-107 (1996).
Luscher, "Endogenous and exogenous nitrates and their role in myocardial ischaemia," Br. J. Clin. Pharmacol. 34:29S-35S (1992).
Shiraki et al., "The Hypotensive Mechanisms of the New Anti-Anginal Drug, N-(2-hydroxyethyl)nicotinamide nitrate (SG-75) in Beagle Dogs," Japan J. Pharmacol. 31:921-929 (1981).
Slart et al., "Nitrate Administration Increases Blood Flow in Dysfunctional but Viable Myocardium, Leading to Improved Assessment of Myocardial Viability: A PET Study," J Nucl Med 47:1307-1311 (2006).
Fayers et al., "Nitrate tolerance and the links with endothelial dysfunction and oxidative stress," Br J Clin Pharmacol 56:620-628 (2003).
Knot, "Nitrate Tolerance in Hypertension: New Insight Into a Century-Old Problem," Circ Res 93:799-801 (2003).
Schulz et al., "Functional and Biochemical Analysis of Endothelial (Dys)function and NO/cGMP Signaling in Human Blood Vessels with and without Nitroglycerin Pretreatment," Circulation 105:1170-1175 (2002).
Hatanaka et al., "Stereoselective Pharmacokinetics and Pharmacodynamics of Organic Nitrates in Rats," Journal of Pharmacology and Experimental Therapeutics 298:346-353 (2001).
Chabot et al., "Characterization of the vasodilator properties of peroxynitrite on rat pulmonary artery: role of poly (adenosine 5'-diphoshoribose synthase," British Journal of Pharmacology 121:485-490 (1997).

* cited by examiner

BETAINE COMPOUNDS

CROSS REFERENCE TO RELATED APPLICATIONS

This application is a continuation of U.S. Utility patent application Ser. No. 13/468,231 to Ronald Kramer et al. entitled "Amino Acid Compounds" and filed on May 10, 2012, which is a continuation-in-part application of the earlier U.S. Utility Patent Application to Ronald Kramer, et. al. entitled "Amino Acid Compounds," application Ser. No. 12/946,153, filed Nov. 15, 2010, now U.S. Pat. No. 8,178,572. This application is also a continuation of U.S. Utility patent application Ser. No. 13/465,947 to Ronald Kramer et al. entitled "Amino Acid Compounds" and filed on May 10, 2012, which is a continuation-in-part application of the earlier U.S. Utility Patent Application to Ronald Kramer, et. al. entitled "Amino Acid Compounds," application Ser. No. 12/946,114, filed Nov. 15, 2010, now U.S. Pat. No. 8,183,288. Application Ser. No. 12/946,114, filed Nov. 15, 2010, now U.S. Pat. No. 8,183,288 and application Ser. No. 12/946,153, filed Nov. 15, 2010, now U.S. Pat. No. 8,178,572, are both continuation applications of the earlier U.S. Utility Patent Application to Ronald Kramer, et. al. entitled "Amino Acid Compounds," application Ser. No. 12/336,938, filed Dec. 17, 2008, now U.S. Pat. No. 8,034,836, which is a continuation application of the earlier U.S. Utility Patent Application to Ronald Kramer, et. al. entitled "Amino Acid Compounds," application Ser. No. 11/950,273, filed Dec. 4, 2007, now U.S. Pat. No. 7,777,074, which application claims the benefit of the filing date of U.S. Provisional Patent Application 60/973,229 entitled "Amino Acid Compounds" to Ronald Kramer, et. al., filed on Sep. 18, 2007. Each of the foregoing applications is hereby incorporated by reference in its entirety.

BACKGROUND

1. Technical Field

Aspects of this document relate generally to amino acid compounds.

2. Background

It is desirable to design new amino acid compounds that have properties lacking in conventional amino acids, conventional nitrates, and conventional nitrites.

SUMMARY

In one aspect, a Nitrate or Nitrite of a Betaine Compound is disclosed. Betaine Compound may be a derivative, an analog, or an isomer of Betaine.

In another aspect, a composition comprising at least one constituent selected from the group consisting of a Nitrate, a Nitrite, and both; and a Betaine Compound is disclosed.

In yet another aspect, a supplement formulation comprising at least one constituent selected from the group consisting of a Nitrate, a Nitrite, and both; and a Betaine Compound is disclosed.

The compositions and supplement formulations may be in a dosage form selected from the group consisting of a capsule, a cachet, a pill, a tablet, a powder, a granule, a pellet, a bead, a particle, a troche, a lozenge, a gel, a liquid, a suspension, a solution, an elixir, and a syrup. The compositions and supplement formulations may further comprise one or more additional components selected from the group consisting of a carrier, an excipient, a binder, a colorant, a flavoring agent, a preservative, a buffer, a dilutant, and any combination thereof.

In certain implementations, the compositions and supplement formulations may be formulated to deliver an effective amount of the constituents to prevent the development of nitrate tolerances, to increase bioabsorption of amino acids, or to increase the vasodilative characteristics of amino acids in a human or animal.

The foregoing and other aspects, features, and advantages will be apparent to those artisans of ordinary skill in the art from the DESCRIPTION and DRAWINGS, and from the CLAIMS.

DESCRIPTION

Overview

Compounds containing both a carboxyl group and an amino group are typically known as Amino Acids. Amino Acids typically have the basic formula X—R, wherein X is:

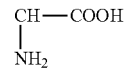

Amino Acids typically differ from one another with respect to the structure of the R group. It is the structure of the R group that typically determines the individuality and character of each Amino Acid.

For example, the R group for the Amino Acid Arginine is:

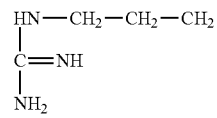

Arginine is characterized as a nonessential Amino Acid. Specifically, Arginine can be independently manufactured by the human body, and does not need to be obtained directly through dietary intake. Arginine plays a significant role in healing, cell division, immune function, the elimination of ammonia from the body and the release of hormones. Arginine is presently used in the dietary supplement industry to supplement Arginine production in the body. Arginine is also presently used in the dietary supplement industry to boost Human Growth Hormone (HGH) production, increase vasodilation, enhance blood circulation, increase oxygen flow to the muscles, and boost Nitric Oxide (NO) production. Various supplemental Arginine forms are available in the consumer marketplace.

The vasodilating effect of ingested Arginine takes considerable time to manifest since Arginine requires extensive metabolism to yield Nitric Oxide (NO). Additionally, considerable amounts of Arginine are required to produce a significant vasodilating effect, with common doses ranging from eight to twenty-four grams per day.

The R group for the Amino Acid Citrulline is:

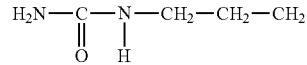

Citrulline is an alpha-Amino Acid naturally occurring in the human body, and does not need to be obtained directly through dietary intake. In vivo, Citrulline is made from the Amino Acid Ornithine, along with carbamoyl phosphate in one of the central reactions in the Urea Cycle. Citrulline is also produced during the metabolism of Arginine in the body. Citrulline is presently used in the dietary supplement industry to supplement Citrulline production in the body. By itself, Citrulline has no vasodilating properties. Citrulline is also water insoluble, which reduces its bioavailability and limits the forms in which Citrulline may be effectively used.

The R group for the Amino Acid Creatine is:

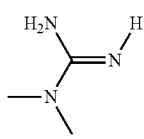

Creatine is a nonessential Amino Acid and is also a nitrogenous organic acid. Creatine is independently manufactured by the human body, and does not need to be obtained directly through dietary intake. Creatine plays a significant role in providing muscles with energy. Creatine is presently used in the dietary supplement industry to supplement Creatine production in the body. Creatine is also presently used in the dietary supplement industry to increase muscle-mass gains, improve athletic performance and strength. Creatine, by itself, has no vasodilating properties. Creatine is also water insoluble, which reduces its bioavailability and limits the forms in which Creatine may be effectively used.

The R group for the Amino Acid Glutamine is:

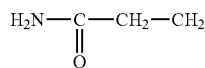

Glutamine is a nonessential Amino Acid. Glutamine is the most abundant naturally occurring, non-essential amino acid in the human body and is found circulating in the blood, as well as stored in the skeletal muscles. Glutamine plays a significant role in protein synthesis, muscle growth, and wound healing. Glutamine is presently used in the dietary supplement industry to supplement Glutamine production in the body. Glutamine is also presently used in the dietary supplement industry to maintain the body's Glutamine pool. Glutamine, by itself, has no vasodilating properties. Glutamine is also water insoluble, which reduces its bioavailability and limits the forms in which Glutamine may be effectively used. Additionally, Glutamine inhibits Nitric Acid (NO) production through downregulation of eNOS synthase.

The R group for the Amino Acid Leucine is:

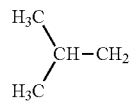

Leucine is an essential Amino Acid, meaning that Leucine is not synthesized in vivo in animals. Accordingly, Leucine must be ingested, usually as a component of proteins consumed directly through dietary intake. Leucine plays a significant role in muscle protein synthesis. Leucine can also inhibit protein degradation in skeletal muscle, as well as in the liver. Leucine is presently used in the dietary supplement industry to supplement dietary Leucine sources. Leucine is also presently used in the dietary supplement industry to promote anabolism and stimulate muscle protein synthesis. Leucine, by itself, has no vasodilating properties. Leucine is also water insoluble, which reduces its bioavailability and limits the forms in which Leucine may be effectively used.

The R group for the Amino Acid Norvaline is:

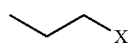

Norvaline is a nonessential Amino Acid. Specifically, Norvaline can be independently manufactured by the human body, and does not need to be obtained directly through dietary intake. Norvaline is presently used in the dietary supplement industry to supplement Norvaline production in the body. Norvaline is also presently used in the dietary supplement industry to inhibit the enzyme arginase and thus reduce the conversion of Arginine to urea. Norvaline, by itself, has no vasodilating properties, although it enhances the vasodilating properties of Arginine. Norvaline is also water insoluble, which reduces its bioavailability and limits the forms in which Leucine may be effectively used.

The R group for the Amino Acid Ornithine is:

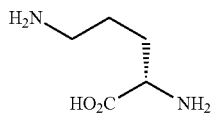

Ornithine is a non-essential Amino Acid. That is, Ornithine is independently manufactured by the human body, and does not need to be obtained directly through dietary intake. Ornithine plays a significant role in the synthesis of polyamines, specifically via the action of Ornithine decarboxylase. Ornithine is presently used in the dietary supplement industry to supplement dietary Ornithine sources. Ornithine is also presently used in the dietary supplement industry to enhance the vasodilating properties in a series of products commonly known as "NO Boosters." Ornithine exerts its vasodilating effect only by in vivo conversion to Arginine and then by following the pathway that converts Arginine to Nitric Acid (NO). Many grams of Ornithine, and a considerable amount of time, are required in order to assert its vasodilating effect.

The R group for the Amino Acid Histidine is:

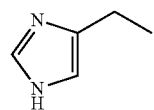

Histidine is a naturally-occurring Amino Acid and is coded for in DNA. Relatively small shifts in cellular pH will change the electrical charge of Histidine. For this reason, Histidine finds its way into considerable use as a coordinating ligand in metalloproteins, and also as a catalytic site in certain enzymes. Histidine is currently used in the dietary supplement industry to support carnosine production. Histidine, by itself, has no vasodilating properties. Additionally, Histidine is very poorly water soluble, a fact that limits its bioavailability and utility. Histidine is presently used in the dietary supplement industry in the forms of single administration Histidine and Histidine HCl.

The R group for the Amino Acid Beta Alanine is:

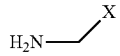

Beta Alanine is the only naturally-occurring Beta Amino Acid. A Beta Amino Acid is one in which the Amino group is located at the beta position (i.e. two atoms away) from the Carboxyl group. Beta Alanine is formed in vivo through the degradation of dihydrouracil and carnosine. Beta Alanine is the rate-limiting precursor of carnosine. Therefore, carnosine levels are limited by the amount of available Beta Alanine Beta Alanine, by itself, has no vasodilating properties. Additionally, Beat Alanine is poorly water soluble, which limits its bioavailability and utility. Beta Alanine is presently used in the dietary supplement industry to support carnosine production.

The chemical structure of Agmatine is:

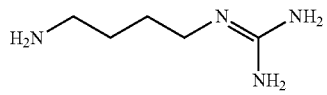

Agmatine is the decarboxylation product of the Amino Acid Arginine and is an intermediate in polyamine biosynthesis. Agmatine is synthesized in the brain and stored in synaptic vesicles in regionally selective neurons. Agmatine is released by depolarization and is inactivated by agmatinase. Agmatine binds to alpha2-adrenoceptors and imidazoline binding sites. Agmatine likewise blocks N-methyl-D-aspartic acid (NMDA) receptor channels and other ligand-gated cationic channels. Additionally, agmatine inhibits nitric oxide synthase, and induces the release of some peptide hormones. Agmatine modulates nitric oxide through various mechanisms. Agmatine stimulates some types of nitric oxide synthase (NOS) while inhibiting others. Agmatine inhibits Nitric Oxide production by inhibiting NOS. Agmatine is presently used in the dietary supplement industry in the forms of single administration Agmatine and Agmatine Sulfate.

In addition, many Amino Acid derivatives and products of Amino Acid biosynthesis themselves may have biological and physiological effects.

For example, Carnitine is a quaternary ammonium compound biosynthesized from the amino acids lysine and methionine. Acetyl-L-Carnitine is an alternative form of carnitine with an acetyl group coupled with the hydroxyl group of the third carbon molecule. Propionyl-L-carnitine is another alternative form of carnitine that contains a propionyl group coupled with the third carbon molecule. The chemical structures of Carnitine, Acetyl-L-Carnitine, and Propionyl-L-carnitine are as follows:

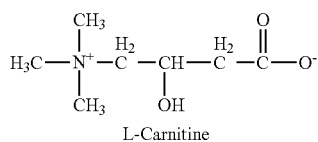

L-Carnitine

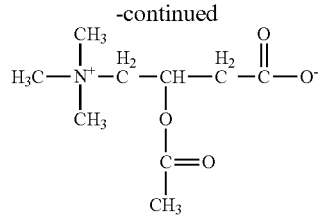

Acetyl-L-Carnitine

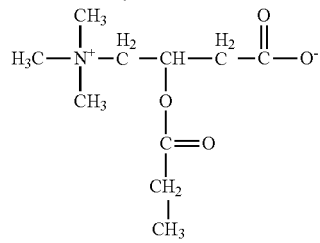

Propionyl-L-Carnitine

Significantly, neither carnitine nor its alternative forms possess vasodilating properties. In addition, since carnitine and its alternative forms are bipolar molecules, their solubility might be lowered with respect to pH. Carnitine is presently used in the dietary supplement industry to supplement Carnitine production in the body. Carnitine is also presently used in the dietary supplement industry to improve athletic performance, enhance mood, and boost immune response. Various supplemental Carnitine forms are available in the consumer marketplace.

As another example, Taurine is a derivative of the sulfur-containing amino acid Cysteine. Taurine by itself has no vasodilating properties. Taurine is presently used in the dietary supplement industry to supplement Taurine production in the body. Taurine is also presently used in the dietary supplement industry to improve athletic performance and resist muscle cramps. Various supplemental Taurine forms are available in the consumer marketplace, including many sports supplements and energy drinks.

As still another example, Betaine (also known as Trimethyl Glycine, 2-trimethylammonioacetate, glycine betaine, betaine anhydrous, and N,N,N-trimethylglycine) is a derivative of Glycine. Betaine is an N-trimethylated amino acid. This quaternary ammonium exists as the zwitterion at neutral pH. Betaine can be easily produced by mixing Glycine with methyl iodide. The structure of Betaine is:

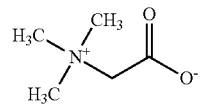

Nitrates are a class of compounds that are salts of Nitric Acid ($HNO_3$) and at least comprise one Nitrogen atoms and three Oxygen atoms ($NO_3$). Nitrites are a class of compounds that are salts of Nitrous Acid ($HNO_2$) and at least comprise one Nitrogen atom and two Oxygen atoms ($NO_2$).

Nitrates and Nitrites are commercially available in various preparations and are used in various commercial applications. In the case of ingestion by humans, Nitrate ($NO_3$) is typically reduced to Nitrite ($NO_2$) in the epithelial cells of blood vessels. In vivo, Nitrite ($NO_2$) reacts with a thiol donor, principally glutathione, to yield Nitric Oxide (NO).

TERMINOLOGY AND DEFINITIONS

In describing implementations of an Amino Acid Compound, the following terminology will be used in accordance with the definitions and explanations set out below. Notwithstanding, other terminology, definitions, and explanations may be found throughout this document, as well.

As used herein, "Amino Acid" is a term used in its broadest sense and may refer to an Amino Acid in its many different chemical forms including a single administration Amino Acid, its physiologically active salts or esters, its combinations with its various salts, its tautomeric, polymeric and/or isomeric forms, its analog forms, its derivative forms, and/or its decarboxylation products. Amino Acids comprise, by way of non-limiting example: Agmatine, Beta Alanine, Arginine, Asparagine, Aspartic Acid, Cysteine, Glutamine, Glutamic Acid, Glycine, Histidine, Isoleucine, Leucine, Lysine, Methionine, PhenylBeta Alanine, Proline, Serine, Threonine, Tryptophan, Tyrosine, and Valine.

As used herein, "Compound" is a term used in its broadest sense and may refer to an Amino Acid in combination with one of a Nitrate and a Nitrite.

As used herein, "Nitrate" is a term used in its broadest sense and may refer to an Nitrate in its many different chemical forms including a salt of Nitric Acid, a single administration Nitrate, its physiologically active salts or esters, its combinations with its various salts, its tautomeric, polymeric and/or isomeric forms, its analog forms, and/or its derivative forms. Nitrate comprises, by way of non-limiting example, many different chemical forms including dinitrate and trinitrate. Nitrates may be salts, or mixed salts, of Nitric Acid and comprise one Nitrogen atom and three Oxygen atoms. For the exemplary purposes of this disclosure, Nitrate may comprise salts of Nitrate such as sodium nitrate, potassium nitrate, barium nitrate, calcium nitrate, and the like. For the exemplary purposes of this disclosure, Nitrate may include mixed salts of Nitrate such as nitrate orotate, and the like. Additionally, for the exemplary purposes of this disclosure, Nitrate may comprise nitrate esters such as nitroglycerine, and the like.

As used herein, "Nitrite" is a term used in its broadest sense and may refer to an Nitrite in its many different chemical forms including a salt of Nitrous Acid, a single administration Nitrite, its physiologically active salts or esters, its combinations with its various salts, its tautomeric, polymeric and/or isomeric forms, its analog forms, and its derivative forms. Nitrite comprises, by way of non-limiting example, many different chemical forms including dinitrite and trinitrite. Nitrites may be salts, or mixed salts, of Nitrous Acid and comprise one Nitrogen atom and two Oxygen atoms. For the exemplary purposes of this disclosure, Nitrite may comprise salts of Nitrite such as sodium nitrite, potassium nitrite, barium nitrite, calcium nitrite, and the like. For the exemplary purposes of this disclosure, Nitrite may comprise mixed salts of Nitrite such as nitrite orotate, and the like. Additionally, for the exemplary purposes of this disclosure, Nitrite may comprise nitrite esters such as amyl nitrite, and the like.

As used herein, "pharmaceutically acceptable additive" or "additive" are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmelose cellulose, magnesium stearate, and silicon dioxide.

As used in this document, "pharmaceutically effective" is a phrase used in its broadest sense, including, by non-limiting example, effective in a clinical trial, for a specific patient, or only placebo-effective.

As used in this document, "Pharmaceutically acceptable" is a phrase used in its broadest sense and may describe ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

Compounds/Components

A first implementation is an Arginine compound of the formula:

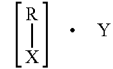

wherein;
R is the Arginine group identified and defined above;
X is the Amino Acid base identified and defined above; and
Y is selected from the group consisting of a Nitrate and a Nitrite.

Applicants have cost-effectively synthesized Arginine Nitrate by combining nitric acid and Arginine, mixing with water, and leaving to crystallize. Further nitratization can take place, yielding Arginine Dinitrate or Arginine Trinitrate. An alternative implementation may comprise using Nitrous Acid ($HNO_2$) instead of Nitric Acid ($HNO_3$), thus yielding Arginine Nitrite. Arginine Nitrite has the same effects as Arginine Nitrate, the only difference being that it requires one less step to yield Nitric Oxide (NO—). Mixed salts may also be used, such as in the non-limiting example of Arginine Nitrate-Orotate.

A second implementation is a Citrulline compound of the formula:

wherein;
R is the Citrulline group identified and defined above;
X is the Amino Acid base identified and defined above; and Y is selected from the group consisting of a Nitrate and a Nitrite.

Applicants have cost-effectively synthesized Citrulline Nitrate by combining nitric acid and Citrulline, mixing with water, and leaving to crystallize. Further nitratization can take place, yielding Citrulline Dinitrate or Citrulline Trinitrate. An alternative implementation may comprise using Nitrous Acid ($HNO_2$) instead of Nitric Acid ($HNO_3$), thus yielding Citrulline Nitrite. Citrulline Nitrite has the same effects as Citrulline Nitrate, the only difference being that it requires one less step to yield Nitric Oxide (NO—). Mixed salts may also be used, such as in the non-limiting example of Citrulline Nitrate-Orotate.

A third implementation is a Creatine compound of the formula:

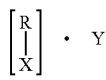

wherein;
R is the Creatine group identified and defined above;
X is the Amino Acid base identified and defined above; and
Y is selected from the group consisting of a Nitrate and a Nitrite.

Applicants have cost-effectively synthesized Creatine Nitrate by combining nitric acid and Creatine, mixing with water, and leaving to crystallize. Further nitratization can take place, yielding Creatine Dinitrate or Creatine Trinitrate. An alternative implementation may comprise using Nitrous Acid ($HNO_2$) instead of Nitric Acid ($HNO_3$), thus yielding Creatine Nitrite. Creatine Nitrite has the same effects as Creatine Nitrate, the only difference being that it requires one less step to yield Nitric Oxide (NO—). Mixed salts may also be used, such as in the non-limiting example of Creatine Nitrate-Orotate.

A fourth implementation is a Glutamine compound of the formula:

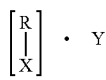

wherein;
R is the Glutamine group identified and defined above;
X is the Amino Acid base identified and defined above; and
Y is selected from the group consisting of a Nitrate and a Nitrite.

Applicants have cost-effectively synthesized Glutamine Nitrate by combining nitric acid and Glutamine, mixing with water, and leaving to crystallize. Further nitratization can take place, yielding Glutamine Dinitrate or Glutamine Trinitrate. An alternative implementation comprises using Nitrous Acid ($HNO_2$) instead of Nitric Acid ($HNO_3$), thus yielding Glutamine Nitrite. Glutamine Nitrite has the same effects as Glutamine Nitrate, the only difference being that it requires one less step to yield Nitric Oxide (NO—). Mixed salts may also be used, such as in the non-limiting example of Glutamine Nitrate-Orotate.

A fifth implementation is a Leucine compound of the formula:

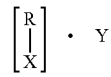

wherein;
R is the Leucine group identified and defined above;
X is the Amino Acid base identified and defined above; and
Y is selected from the group consisting of a Nitrate and a Nitrite.

Applicants have cost-effectively synthesized Leucine Nitrate by combining nitric acid and Leucine, mixing with water, and leaving to crystallize. Further nitratization can take place, yielding Leucine Dinitrate or Leucine Trinitrate. An alternative implementation comprises substituting the Amino Acids Valine or Isoleucine for Leucine. Another alternative implementation comprises substituting Nitrous Acid ($HNO_2$) for Nitric Acid ($HNO_3$), thus yielding Leucine Nitrite. Leucine Nitrite has the same effects as Leucine Nitrate, the only difference being that it requires one less step to yield Nitric Oxide (NO—). Mixed salts may also be used, such as in the non-limiting example of Leucine Nitrate-Orotate.

A sixth implementation is a Norvaline compound of the formula:

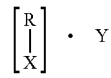

wherein;
R is the Norvaline group identified and defined above;
X is the Amino Acid base identified and defined above; and
Y is selected from the group consisting of a Nitrate and a Nitrite.

Applicants have cost-effectively synthesized Norvaline Nitrate by combining nitric acid and Norvaline, mixing with water, and leaving to crystallize. Further nitratization can take place, yielding Norvaline Dinitrate or Norvaline Trinitrate. An alternative implementation comprises substituting Nitrous Acid ($HNO_2$) for Nitric Acid ($HNO_3$), thus yielding Norvaline Nitrite. Norvaline Nitrite has the same effects as Norvaline Nitrate, the only difference being that it requires one less step to yield Nitric Oxide (NO—). Mixed salts may also be used, such as in the non-limiting example of Norvaline Nitrate-Orotate.

A seventh implementation is an Ornithine compound of the formula:

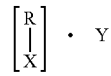

wherein;
R is the Ornithine group identified and defined above;
X is the Amino Acid base identified and defined above; and
Y is selected from the group consisting of a Nitrate and a Nitrite.

Applicants have cost-effectively synthesized Ornithine Nitrate by combining nitric acid and Ornithine, mixing with water, and leaving to crystallize. Further nitratization can take place, yielding Ornithine Dinitrate or Ornithine Trinitrate. An alternative implementation comprises using Nitrous Acid (HNO$_2$) instead of Nitric Acid (HNO$_3$), thus yielding Ornithine Nitrite. Ornithine Nitrite has the same effects as Ornithine Nitrate, the only difference being that it requires one less step to yield Nitric Oxide (NO—). Mixed salts may also be used, such as in the non-limiting example of Ornithine Nitrate-Orotate.

An eighth implementation is a Histidine compound of the formula:

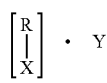

wherein;
R is the Histidine group identified and defined above;
X is the Amino Acid base identified and defined above; and
Y is selected from the group consisting of a Nitrate and a Nitrite.

Applicants have cost-effectively synthesized Histidine Nitrate by combining nitric acid and Histidine, mixing with water, and leaving to crystallize. Further nitratization can take place, yielding Histidine Dinitrate or Histidine Trinitrate. An alternative implementation comprises using Nitrous Acid (HNO$_2$) instead of Nitric Acid (HNO$_3$), thus yielding Histidine Nitrite. Histidine Nitrite has the same effects as Histidine Nitrate, the only difference being that it requires one less step to yield Nitric Oxide (NO—). Mixed salts may also be used, such as in the non-limiting example of Histidine Nitrate-Orotate.

A ninth implementation is a Beta Alanine compound of the formula:

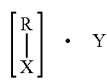

wherein;
R is the Beta Alanine group identified and defined above;
X is the Amino Acid base identified and defined above; and
Y is selected from the group consisting of a Nitrate and a Nitrite.

Applicants have cost-effectively synthesized Beta Alanine Nitrate by combining nitric acid and Beta Alanine, mixing with water, and leaving to crystallize. Further nitratization can take place, yielding Beta Alanine Dinitrate or Beta Alanine Trinitrate. An alternative implementation comprises using Nitrous Acid (HNO$_2$) instead of Nitric Acid (HNO$_3$), thus yielding Beta Alanine Nitrite. Beta Alanine Nitrite has the same effects as Beta Alanine Nitrate, the only difference being that it requires one less step to yield Nitric Oxide (NO—). Mixed salts may also be used, such as in the non-limiting example of Beta Alanine Nitrate-Orotate.

A tenth implementation is an Agmatine compound of the formula:

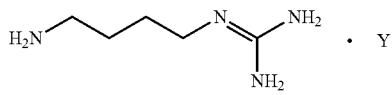

wherein;
Y is selected from the group consisting of a Nitrate and a Nitrite.

Applicants have cost-effectively synthesized Agmatine Nitrate by combining nitric acid and Agmatine, mixing with water, and leaving to crystallize. Further nitratization can take place, yielding Agmatine Dinitrate or Agmatine Trinitrate. An alternative implementation comprises using Nitrous Acid (HNO$_2$) instead of Nitric Acid (HNO$_3$), thus yielding Agmatine Nitrite. Agmatine Nitrite has the same effects as Agmatine Nitrate, the only difference being that it requires one less step to yield Nitric Oxide (NO—). Mixed salts may also be used, such as in the non-limiting example of Agmatine Nitrate-Orotate.

A first implementation is a Carnitine compound of the formula:

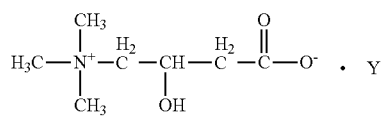

wherein;
Y is selected from the group consisting of a Nitrate and a Nitrite.

Applicants have cost-effectively synthesized Carnitine Nitrate by combining nitric acid and Carnitine, mixing with water, and leaving to crystallize. Further nitratization can take place, yielding Carnitine Dinitrate or Carnitine Trinitrate. An alternative implementation may comprise using Nitrous Acid (HNO$_2$) instead of Nitric Acid (HNO$_3$), thus yielding Carnitine Nitrite. Carnitine Nitrite has the same effects as Carnitine Nitrate, the only difference being that it requires one less step to yield Nitric Oxide (NO—). Mixed salts may also be used, such as in the non-limiting example of Carnitine Nitrate-Orotate. In addition, it will be understood that alternative implementations comprising Acetyl-L-Carnitine and/or Propionyl-L-carnitine in combination with one of a Nitrate and a Nitrite are likewise possible in accordance with these disclosures.

Another implementation is a Taurine compound of the formula:

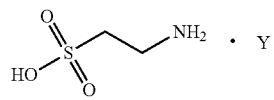

wherein;
Y is selected from the group consisting of a Nitrate and a Nitrite.

Applicants have cost-effectively synthesized Taurine Nitrate by combining nitric acid and Taurine, mixing with water, and leaving to crystallize. Further nitratization can take place, yielding Taurine Dinitrate or Taurine Trinitrate. An alternative implementation may comprise using Nitrous Acid (HNO$_2$) instead of Nitric Acid (HNO$_3$), thus yielding Taurine Nitrite. Taurine Nitrite has the same effects as Taurine Nitrate, the only difference being that it requires one less step to yield Nitric Oxide (NO—). Mixed salts may also be used, such as in the non-limiting example of Taurine Nitrate-Orotate.

Still another implementation is a Betaine compound of the formula:

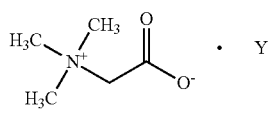

wherein;
Y is selected from the group consisting of a Nitrate and a Nitrite.

Applicants have cost-effectively synthesized Betaine Nitrate by combining nitric acid and Betaine, mixing with water, and leaving to crystallize. Further nitratization can take place, yielding Betaine Dinitrate or Betaine Trinitrate. An alternative implementation comprises using Nitrous Acid ($HNO_2$) instead of Nitric Acid ($HNO_3$), thus yielding Betaine Nitrite. Betaine Nitrite has the same effects as Betaine Nitrate, the only difference being that it requires one less step to yield Nitric Oxide (NO—). Mixed salts may also be used, such as in the non-limiting example of Betaine Nitrate-Orotate.

Compositions and/or formulations may be administered in any form, including one of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, and combinations thereof for example. Compositions and/or formulations may also include a acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

Implementations of Amino Acid Nitrate and/or Nitrite Compounds may also be synthesized or created in a wide variety of manners, and may be made from a wide variety of materials. Those of ordinary skill in the art will readily be able to select appropriate materials and methods to manufacture and use the compounds disclosed herein.

Dosage Forms

Implementations of Amino Acid Compounds may conveniently be presented in unit dosage form. Unit dosage formulations may be those containing a daily dose or unit, a daily sub-dose, or an appropriate fraction thereof, of the administered components as described herein.

A dosage unit may include an Amino Acid Compound. In addition, a dosage unit may include an Amino Acid Compound admixed with a pharmaceutically acceptable additive(s), and/or any combination thereof.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes.

For the exemplary purposes of this disclosure, oral delivery may be a particularly advantageous delivery route for administration to humans and animals of implementations of a pharmaceutical composition, optionally formulated with appropriate pharmaceutically acceptable additives to facilitate administration.

Manufacture

Implementations of an Amino Acid Compound may be made using conventional or other procedures. Accordingly, although there are a variety of method implementations for producing pharmaceutical compositions, for the exemplary purposes of this disclosure, a method implementation for producing an Amino Acid Compound may comprise: measuring specific quantities of Amino Acid, Nitric or Nitrous Acid and water mixed in a specific order the measured quantities of Amino Acid, Nitric or Nitrous Acid and water, and any additional pharmaceutically acceptable additives or inert ingredients, and then separating the pharmaceutical composition into discrete quantities for distribution and/or administration.

Measuring specific quantities of Amino Acid, Nitric or Nitrous Acid and water, and pharmaceutically acceptable additives or inert ingredients, may involve any number of steps and implementing components, and measuring specific quantities of Amino Acid, Nitric or Nitrous Acid and water, and pharmaceutically acceptable additives or inert ingredients, may be accomplished readily from this disclosure. For the exemplary purposes of this disclosure, measuring specific quantities of Amino Acid, Nitric or Nitrous Acid and water, and pharmaceutically acceptable additives or inert ingredients, may comprise using a scale, a solid or liquid dispensing apparatus, or other measurement device capable of measuring solid mass or liquid volume to produce a desired quantity of Amino Acid, Nitric or Nitrous Acid and water, and pharmaceutically acceptable ingredient.

It should be appreciated that any of the components of particular implementations of an Amino Acid Compound may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion Compoundation, lyophilization, melting, mixed, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Mixing the measured quantities of Amino Acid, Nitric or Nitrous Acid and water, and pharmaceutically acceptable additives or inert ingredients, may involve any number of steps and implementing components, and may be accomplished readily from this disclosure. For the exemplary purposes of this disclosure, mixed the measured quantities of Amino Acid, Nitric or Nitrous Acid and water, and pharmaceutically acceptable additives or inert ingredients, may comprise combining the measured quantities of m Amino Acid, Nitric or Nitrous Acid and water, and pharmaceutically acceptable additives or inert ingredients, under the influence of physical, ultrasonic, or electrostatic forces to create a desired degree of intermingling and/or chemical reaction of the Amino Acid, Nitric or Nitrous Acid and water and any pharmaceutically acceptable ingredients. The mixed may be accomplished when the Amino Acid, Nitric or Nitrous Acid and water and/or any pharmaceutically acceptable ingredients are in a solid, liquid, or semisolid state.

Separating the Amino Acid Compound into discrete quantities for distribution may involve any number of steps and implementing components, and separating the Amino Acid Compound into discrete quantities for distribution may be accomplished readily from this disclosure. For the exemplary purposes of this disclosure, separating the Amino Acid Compound into discrete quantities for distribution may involve utilizing a specific piece of equipment, for example, a conventional tablet forming apparatus to shape the formed composition into individual tablets, each containing a desired dose of Amino Acid Compound. The separating process may be accomplished when the Amino Acid Compound is in a solid, liquid, or semisolid state.

Those of ordinary skill in the art will be able to readily select manufacturing equipment and pharmaceutically acceptable additives or inert ingredients to manufacture implementations of an Amino Acid Compound. For the exemplary purposes of this disclosure, some examples of pharmaceutically acceptable additives or inert ingredients and manufacturing process are included below, particularly those that relate to manufacture of implementations of an Amino Acid Compound in tablet form. Notwithstanding the specific examples given, it will be understood that those of ordinary skill in the art will readily appreciate how to manufacture implementations of an Amino Acid Compound according to the other methods of administration and delivery disclosed in this document.

A particular implementation of an Amino Acid Compound may include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of an Amino Acid Compound may also include a binder. Binders are any agents used to impart cohesive qualities to powdered material through particle-particle bonding. Binders may include, for example, matrix binders (e.g. dry starch, dry sugars), film binders (e.g. celluloses, bentonite, sucrose), and chemical binders (e.g. polymeric cellulose derivatives, such as methyl cellulose, carboxy methyl cellulose, and hydroxy propyl cellulose); and other sugar, gelatin, non-cellulosic binders and the like.

Disintegrators may be used in particular implementations of an Amino Acid Compound to facilitate the breakup or disintegration of tablets after administration. Disintegrators may include, for example, starch, starch derivatives, clays (e.g. bentonite), algins, gums (e.g. guar gum), cellulose, cellulose derivatives (e.g. methyl cellulose, carboxymethyl cellulose), croscarmellose sodium, croscarmellose cellulose, and other organic and inorganic materials.

Implementations of an Amino Acid Compound may include diluents, or any inert substances added to increase the bulk of the Amino Acid Compound to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in an Amino Acid Compound and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

Implementations of an Amino Acid Compound may also be administered through use of amphipathic lipid delivery systems (such as liposomes and unilamellar vesicles), caplet systems, oral liquid systems, parenteral and/or intravenous systems, topical systems (creams, gels, transdermal patches, etc.), intranasal systems, rectal or vaginal systems, and many other delivery methods and/or systems known to those of ordinary skill in the art. Those of ordinary skill in the art will readily be able to select additional pharmaceutically acceptable additives to enable delivery of implementations of a pharmaceutical composition from the disclosure in this document.

With respect to delivery of particular implementations of an Amino Acid Compound, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, rectangular or triangular, for example. The tablets may be optionally scored so that they may be separated into different dosages. They may differ greatly in size and weight depending on the amount of the pharmaceutically acceptable active agent or agents present and the intended route of administration. They are divided into two general classes, (1) compressed tablets, and (2) molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multi-particulate composition, a coated multi-particulate composition, an ion-exchange resin-based composition, an osmosis-based composition, or a biodegradable polymeric composition.

While manufacture of implementations of an Amino Acid Compound have been described in particular sequences of steps and/or in particular forms, it will be understood that such manufacture is not limited to the specific order of steps or forms as disclosed. Any steps or sequences of steps of manufacture of implementations of an Amino Acid Compound in any form are given as examples of possible steps or sequences of steps or potential forms and not as limitations, since many possible manufacturing processes and sequences of steps may be used to manufacture Amino Acid Compound implementations in a wide variety of forms.

Use

Implementations of an Amino Acid Compound are particularly useful in increasing vasodilation and blood flow in humans and animals. However, implementations are not limited to uses relating to vasodilation modification, and the like. Rather, any description relating to the foregoing is for the exemplary purposes of this disclosure. It will be understood that implementations of an Amino Acid Compound may encompass a variety of uses and are not limited in their uses. For example, possible uses may be, by non-limiting example, prevention of Nitrate tolerance, enhanced water solubility, increased distribution to muscles, improved athletic performance, faster action than single-administration, and/or countering Nitric Oxide inhibiting effects of certain Amino Acids.

In conventional preparations of Nitrate compounds, "tolerance," a particular side effect, has been observed in many patients. This is unfortunate because the effectiveness of Nitrate on vasodilation is well documented. "Tolerance" occurs when a subject's reaction to Nitrate decreases so that larger doses are required to achieve the same effect. A Mar. 3, 2000 report in the British Journal of Pharmacology indicates that "tolerance to the dilator effects of nitrates remains a persisting therapeutic problem." Raymond J. MacAllister "Arginine and Nitrate Tolerance" available at http://www.nature.com/bjp/journal/v130/n2/full/0703340a.html, the contents of which are hereby incorporated herein by reference.

Empirical studies indicate that Nitrates are useful for their vasolidating effects. Common Nitrates include nitroglycerin and isosorbide dinitrate. Nitrates exert their vasodilating effect through their reduction to Nitrites. In vivo, Nitrates are reduced to Nitrites and, in the blood vessels' epithelial cells, Nitrite reacts with a thiol donor (mainly glutathione) to yield Nitric Oxide. Louis J. Ignarro, "After 130 years, the Molecular Mechanism of Action of Nitroglycerin is Revealed" (Jun. 11, 2002) available at http://www.pnas.org/cgi/content/full/99/12/7816?ck=nck, the contents of which are hereby incorporated herein by reference.

The Nitric Oxide inhibiting characteristics of the Amino Acid Glutamine have been well documented in a number of studies. In particular, a Mar. 28, 2006 report in the American Journal of Physiology has found that Glutamine inhibits Nitric Oxide production by downregulation of eNOS synthase. Masao Kakoki, et al. "Amino acids as Modulators of Endothelium-Derived Nitric Oxide." available at http://ajprenal.physiology.org/cgi/content/full/291/2/F297, the contents of which are hereby incorporated by reference.

A January 2006 *Journal of Nutrition* report indicates that the Amino Acid Leucine promotes anabolism and stimulates muscle protein synthesis. Michael J. Rennie, et al. "Branched-Chain Amino Acids as Fuels and Anabolic Signals in Human Muscle" available at http://jn.nutrition.org/cgi/content/full/136/1/264S, the contents of which are hereby incorporated by reference.

Empirical studies indicate that the Amino Acid Norvaline inhibits the enzyme arginase and thus decreases the rate of conversion of the Amino Acid Arginine to urea. Takeyori Saheki, et al. "Regulation of Urea Synthesis in Rat Liver" available at http://jb.oxfordjournals.org/cgi/content/abstract/86/3/745?ijkey=5d134456b7443ca36c809269462276e532549798&keytype2=tf_ipsecsha, the contents of which are hereby incorporated by reference.

An October 2004 *Journal of Nutrition* report indicates that the Amino Acid Ornithine promotes anabolism and stimulates muscle protein synthesis. Michael J. Rennie, et al. "Branched-Chain Amino Acids as Fuels and Anabolic Signals in Human Muscle" available at http://jn.nutrition.org/cgi/content/full/136/1/264S, the contents of which are hereby incorporated by reference.

Empirical studies indicate that the Amino Acids Beta-Beta Alanine and L-Histidine support carnosine production. M. Dunnett, "Influence of Oral Beta-Beta Alanine and L-Histidine Supplementation on the Carnosine Content of the Gluteus Medius" Equine Veterinary Journal Supplement, available at http://www.ncbi.nlm.nih.gov/sites/entrez?Db=pubmed&Cmd=ShowDetailView& TermToSearch=10659307&ordinalpos=4&itool= EntrezSystem2.PEntrez.Pubmed.Pubmed, the contents of which are hereby incorporated by reference.

Empirical studies further indicate that the Amino Acids Beta Alanine and L-Histidine increase muscle power, recuperation and stamina. Yoshihiro Suzuki "High Level of Skeletal Muscle Carnosine Contributes to the Latter Half of Exercise Performance During 30-S Maximal Cycle Ergometer Sprinting" in the Japanese Journal of Physiology, available at http://www.ncbi.nlm.nih.gov/sites/entrez?Db=pubmed&Cmd=ShowDetailView& TermToSearch=12139778&ordinalpos=4&itool= EntrezSystem2.PEntrez.Pubmed.Pubmed_ResultsPanel. Pubmed_RVDocSum, the contents of which are hereby incorporated by reference.

Accordingly, Applicants have discovered that the Arginine compound according to the first implementation, when ingested, provides enhanced Nitric Oxide (NO—) production while providing improved vasodilation effects over single administration of Arginine, the single administration of Nitrates, or the single administration of Nitrites. Improved vasodilation may, in turn, provide better circulation and distribution of Arginine in the body. Absorption may be improved since Amino Acid salts with inorganic acids are much more water soluble than single administration Amino Acids. Applicants have also discovered that the vasodilating effect of Arginine Nitrate manifests faster than that of single-administration Arginine, and as fast as any nitrate, since the $NO_3$— group of the salt requires minimal conversion to yield Nitric Oxide. Additionally a much lesser dose may be required for vasodilation to take place, compared to the single administration of Arginine. Likewise, the development of tolerance to the nitrate component of the molecule may be prevented with the presence of Arginine. Arginine Nitrate may promote vasodilation through production of Nitric Oxide by two different pathways, the Arginine citrullization pathway and the nitrate reduction pathway. Arginine Nitrate may likewise be more water soluble than single administration Arginine.

Accordingly, Applicants have discovered that the Citrulline compound according to the second implementation, when ingested, provides enhanced Nitric Oxide (NO—) production while providing improved vasodilation effects over single administration of Citrulline, the single administration of Nitrates, or the single administration of Nitrites. Improved vasodilation may, in turn, provide better circulation and distribution of Citrulline in the body. Absorption may be improved since Amino Acid salts with inorganic acids are much more water soluble than single administration Amino Acids. Additionally a much lesser dose may be required for vasodilation to take place, compared to the single administration of Citrulline or nitrates. Citrulline Nitrate is likewise more water soluble than single administration Citrulline.

Accordingly, Applicants have discovered that the Creatine compound according to the third implementation, when ingested, provides enhanced Nitric Oxide (NO—) production while providing improved vasodilation effects over single administration of Creatine, the single administration of Nitrates, or the single administration of Nitrites. Improved vasodilation may, in turn, provide better circulation and distribution of Creatine in the body. Absorption may be improved since Amino Acid salts with inorganic acids are much more water soluble than single administration Amino Acids. Additionally a much lesser dose may be required for vasodilation to take place, compared to the single administration of nitrates. Creatine Nitrate is likewise more water soluble than single administration Creatine.

Accordingly, Applicants have discovered that the Glutamine compound according to the fourth implementation, when ingested, counters the Nitric Oxide (NO—) inhibiting characteristics of Glutamine. Absorption of Glutamine may be improved since Amino Acid salts with inorganic acids are much more water soluble than single administration Amino Acids. Additionally a much lesser dose may be required for vasodilation to take place, compared to the single administration of nitrates. Glutamine Nitrate may likewise be more water soluble than single administration Glutamine.

Accordingly, Applicants have discovered that the Leucine compound according to the fifth implementation, when ingested, provides enhanced Nitric Oxide (NO—) production while providing improved vasodilation effects over single administration of Leucine, the single administration of Nitrates, or the single administration of Nitrites. Improved vasodilation may, in turn, provide better circulation and distribution of Leucine in the body. Absorption may be improved since Amino Acid salts with inorganic acids are much more water soluble than single administration Amino Acids. Additionally a much lesser dose may be required for vasodilation to take place, compared to the single administration of nitrates. Leucine Nitrate is likewise more water soluble than single administration Leucine.

Accordingly, Applicants have discovered that the Norvaline compound according to the sixth implementation, when ingested, promotes vasodilation through the inhibition of arginase, while promoting Nitric Oxide formation via the nitrate mechanism. Improved vasodilation may, in turn, provide better circulation and distribution of Norvaline in the body. Absorption may be improved since Amino Acid salts with inorganic acids are much more water soluble than single administration Amino Acids. Additionally a much lesser dose may be required for vasodilation to take place, compared to the single administration of nitrates. Norvaline Nitrate may likewise be more water soluble than single administration Norvaline.

Accordingly, Applicants have discovered that the Ornithine compound according to the seventh implementation, when ingested, provides an additional vasodilation mechanism, reducing the amount of Ornithine needed and the amount of time needed for the vasodilating properties to manifest. Improved vasodilation may, in turn, provide better circulation and distribution of Ornithine in the body. Absorption may be improved since Amino Acid salts with inorganic acids are much more water soluble than single administration Amino Acids. Applicants have also discovered that Ornithine Nitrate begins acting as fast as any other nitrate, since the $NO_3$— group of the salt requires minimal conversion to yield Nitric Oxide. Additionally, a much lesser dose may be required for vasodilation to take place, compared to the single administration of nitrates. Ornithine Nitrate may likewise be more water soluble than single administration Ornithine.

Accordingly, Applicants have discovered that the Histidine compound according to the eighth implementation, when ingested, provides a vasodilation mechanism. Vasodilation may, in turn, provide better circulation and distribution of Histidine in the body. Applicants have likewise discovered that the Histidine compound according to the ninth implementation, when ingested, promotes carnosine production, thus increasing muscle power, endurance and recuperation. Absorption may be improved since Amino Acid salts with inorganic acids are much more water soluble than single administration Amino Acids. Applicants have also discovered that Histidine Nitrate begins acting as fast as any other nitrate, since the $NO_3$— group of the salt requires minimal conversion to yield Nitric Oxide. Additionally, a much lesser dose may be required for vasodilation to take place, compared to the single administration of nitrates. Histidine Nitrate may likewise be more water soluble than single administration Histidine.

Accordingly, Applicants have discovered that the Beta Alanine compound according to the ninth implementation, when ingested, provides vasodilation. Vasodilation may, in turn, provide better circulation and distribution of Beta Alanine in the body. Applicants have likewise discovered that the Beta Alanine compound according to the tenth implementation, when ingested, promotes carnosine production, thus increasing muscle power, endurance and recuperation. Absorption may be improved since Amino Acid salts with inorganic acids are much more water soluble than single administration Amino Acids. Applicants have also discovered that Beta Alanine Nitrate begins acting as fast as any other nitrate, since the $NO_3$— group of the salt requires minimal conversion to yield Nitric Oxide. Additionally, a much lesser dose may be required for vasodilation to take place, compared to the single administration of nitrates. Beta Alanine Nitrate may likewise be more water soluble than single administration Beta Alanine.

Accordingly, Applicants have discovered that the Agmatine compound according to the eighth implementation, when ingested, counteracts the Nitric Oxide inhibiting effect of single administration Agmatine. Absorption may be improved since Amino Acid salts with inorganic acids are much more water soluble than single administration Amino Acids. Applicants have also discovered that Agmatine Nitrate begins acting as fast as any other nitrate, since the $NO_3$— group of the salt requires minimal conversion to yield Nitric Oxide. Agmatine Nitrate may likewise be more water soluble than single administration Agmatine.

Accordingly, Applicants have discovered that the Carnitine compound according to an implementation, when ingested, provides enhanced Nitric Oxide (NO—) production while providing improved vasodilation effects over single administration of Carnitine, the single administration of Nitrates, or the single administration of Nitrites. Improved vasodilation may, in turn, provide better circulation and distribution of Carnitine in the body. Absorption may be improved since Amino Acid derivative salts with inorganic acids may be much more water soluble than single administration Amino Acid derivatives. Applicants have also discovered that the vasodilating effect of Carnitine Nitrate and Taurine Nitrate manifests as fast as any nitrate, since the $NO_3$— group of the salt requires minimal conversion to yield Nitric Oxide. Likewise, the development of tolerance to the nitrate component of the molecule may be prevented with the presence of Carnitine and/or Taurine.

What is claimed is:

1. A Betaine Compound having the structure of:

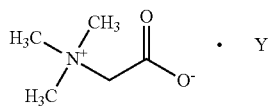

wherein Y is a Nitrate.

2. A composition comprising:
a Nitrate constituent; and
a Betaine Compound having the structure of:

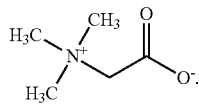

3. The composition of claim 2, wherein the composition is in a dosage form selected from the group consisting of a capsule, a cachet, a pill, a tablet, a powder, a granule, a pellet, a bead, a particle, a troche, a lozenge, a gel, a liquid, a suspension, a solution, an elixir, and a syrup.

4. The composition of claim 2, further comprising one or more additional components selected from the group consisting of a carrier, an excipient, a binder, a colorant, a flavoring agent, a preservative, a buffer, a dilutant, and any combination thereof.

5. The composition of claim 2, wherein the composition is formulated to deliver an effective amount of the constituents to prevent the development of nitrate tolerances, to increase bioabsorption of amino acids, or to increase the vasodilative characteristics of amino acids in a human.

6. The composition of claim 2, wherein the composition comprises an effective amount of the Nitrate constituent; and an effective amount of the Betaine Compound.

7. A supplement formulation comprising:
a Nitrate salt constituent; and
a Betaine Compound having the structure of:

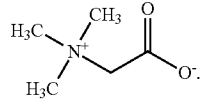

8. The supplement formulation of claim 7, wherein the supplement formulation is in a dosage form selected from the group consisting of a capsule, a cachet, a pill, a tablet, a powder, a granule, a pellet, a bead, a particle, a troche, a lozenge, a gel, a liquid, a suspension, a solution, an elixir, and a syrup.

9. The supplement formulation of claim 7, further comprising one or more additional components selected from the group consisting of a carrier, an excipient, a binder, a colorant, a flavoring agent, a preservative, a buffer, a dilutant, and any combination thereof.

10. The supplement formulation of claim 7, wherein the supplement formulation is formulated to deliver an effective amount of the constituents to prevent the development of nitrate tolerances, to increase bioabsorption of amino acids, or to increase the vasodilative characteristics of amino acids in a human.

11. The supplement formulation of claim 7, wherein the supplement formulation comprises an effective amount of the Nitrate salt constituent, and an effective amount of the Betaine Compound.

* * * * *